United States Patent [19]

Kachigian

[11] Patent Number: 5,084,005
[45] Date of Patent: Jan. 28, 1992

[54] SWAB FOR COLLECTION OF BIOLOGICAL SAMPLES

[75] Inventor: Corrinne S. Kachigian, Flemington, N.J.

[73] Assignee: Becton, Dickinson and Company, Franklin Lakes, N.J.

[21] Appl. No.: 523,441

[22] Filed: May 14, 1990

Related U.S. Application Data

[63] Continuation of Ser. No. 218,714, Jul. 13, 1988, abandoned.

[51] Int. Cl.$^5$ ............................................. A61M 35/00
[52] U.S. Cl. ....................................... 604/1; 128/756; 128/759
[58] Field of Search ..................................... 604/1-3, 604/369; 128/749, 756, 757, 759

[56] References Cited

U.S. PATENT DOCUMENTS

| | | | |
|---|---|---|---|
| 3,228,398 | 1/1966 | Leonard et al. | 604/1 |
| 3,724,018 | 4/1973 | Sills | 15/244 R |
| 3,871,375 | 3/1975 | Bennett | 128/269 |
| 4,027,658 | 6/1977 | Marshall | 128/757 |
| 4,486,109 | 12/1984 | Rosofsky | 604/3 |
| 4,492,305 | 1/1985 | Avery | 206/210 |
| 4,618,576 | 10/1986 | Rosenstein et al. | 435/7 |
| 4,687,746 | 8/1987 | Rosenberg | 128/759 |
| 4,754,764 | 7/1988 | Bayne | 128/759 |
| 4,762,133 | 8/1988 | Bayne et al. | 128/759 |
| 4,800,896 | 1/1989 | Jalowayski | 128/759 |
| 4,935,001 | 6/1990 | George | 604/1 |

FOREIGN PATENT DOCUMENTS

| | | | |
|---|---|---|---|
| 0056493 | 7/1982 | European Pat. Off. | 128/756 |
| 0066958 | 12/1982 | European Pat. Off. | 128/757 |
| 0392560 | 3/1924 | Fed. Rep. of Germany | 604/1 |
| 0002170 | of 1905 | United Kingdom | 604/1 |
| 1332947 | 10/1973 | United Kingdom | |
| 1429689 | 3/1976 | United Kingdom | 128/757 |

Primary Examiner—John D. Yasko
Assistant Examiner—Anthony Gutowski
Attorney, Agent, or Firm—John L. Voellmicke

[57] ABSTRACT

A swab for collection of biological samples comprises a handle having a proximal end and a distal end and a swabbing tip formed of closed cell polymeric foam at the distal end for contacting and collecting biological samples.

25 Claims, 2 Drawing Sheets

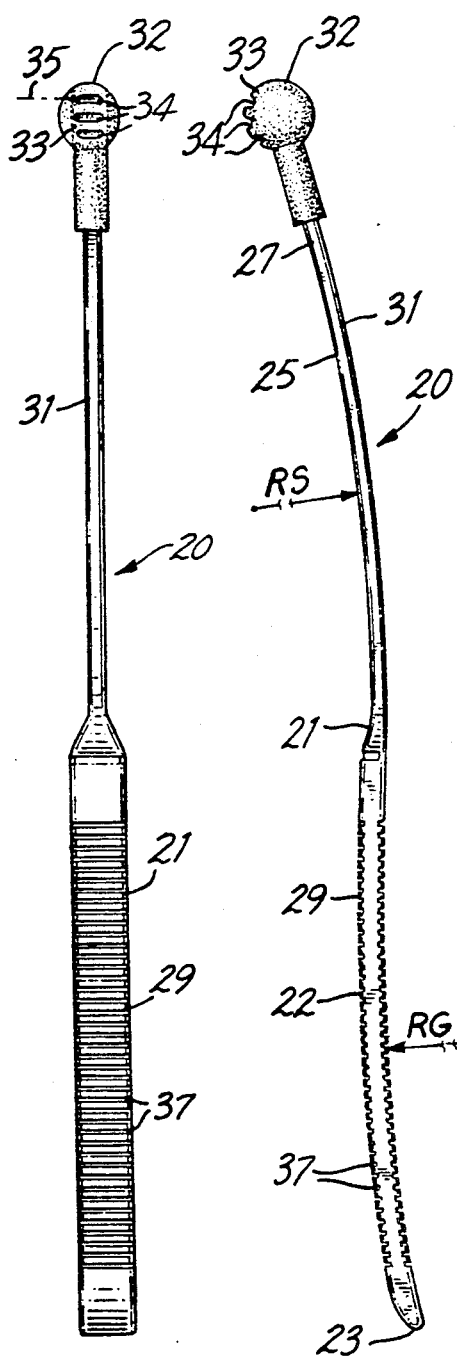
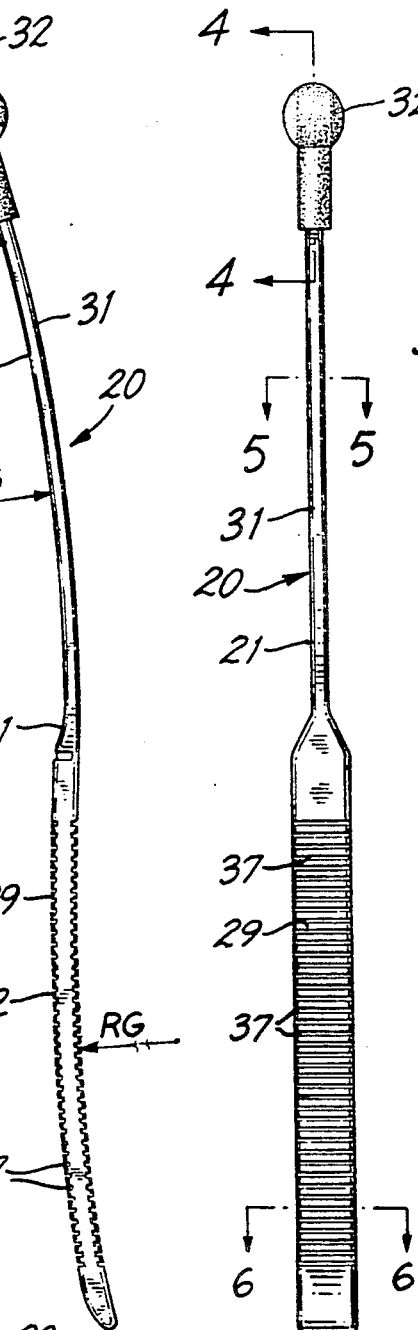
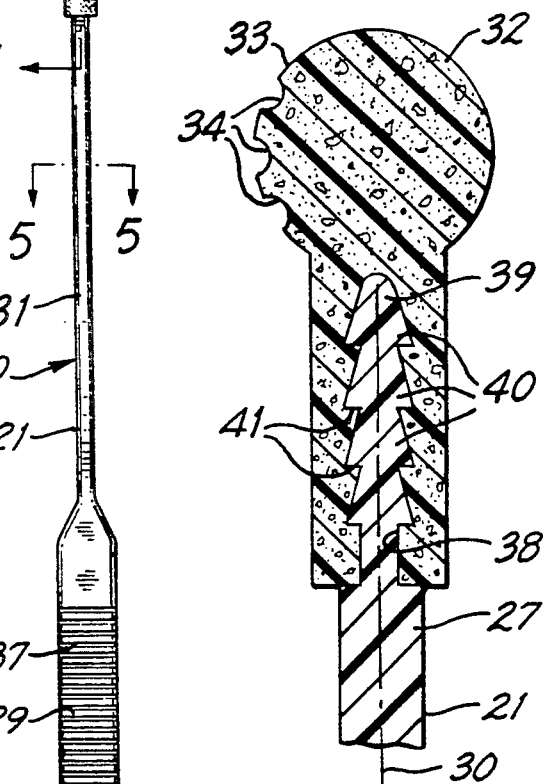
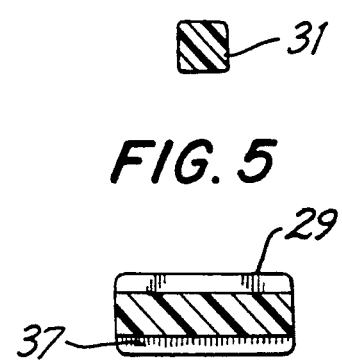
FIG. 1  FIG. 2  FIG. 3
FIG. 4
FIG. 5
FIG. 6

SWAB FOR COLLECTION OF BIOLOGICAL SAMPLES

This is a continuation of application Ser. No. 07/218,714, filed Jul. 13, 1988 (now abandoned).

BACKGROUND OF THE INVENTION

1. Field of the Invention

The present invention relates to swabs for collecting biologcal samples and more particularly concerns a swab having improved handle features and a swabbing tip made of closed cell foam.

2. Description of Related Information

Traditionally, testing for microorganisms such as Streptococcus has been performed by, for example, taking a sample from the patient's throat using a soft tipped swab in order to accumulate as large a sample of the suspected organism as reasonably possible. The organism was then placed in a culture medium and grown until sufficient quantities existed for identification. Swabs used to gather microorganism samples have been made of fibrous materials such as cotton, polyester and rayon, and open pore or open cell foam as taught by Sills in U.S. Pat. No. 3,724,018. The more microorganisms that could be collected the faster the colonies could be grown to sizes necessary to reach a conclusion regarding the presence of specific microorganisms. Accordingly, many swab designs and related accessories have been developed to assure a reasonable sample size and to protect the microorganisms in the time period between sampling and culturing. For example, U.S. Pat. No. 4,492,305 to Avery teaches a culture collection system which attempts to keep the culture alive for a period of time until it is tested. Avery teaches a culture collecting swab and a sealed glass ampoule with a resilient closure member positioned at the stem of the swab. After culture collection the ampoule is broken open, along a score line, and the tip end of the swab is inserted into the ampoule through the open end into culture sustaining media wherein further penetration causes the resilient closure to seal the opening thus defining a culture sustaining environment for the swab and the collected microorganisms until testing.

Although traditional testing and culture growth methods have evolved into more efficient systems there is still a substantial time delay between the specimen collection and the actual determination. When dealing with life threatening or serious health hazards these time delays still present impediments to timely diagnosis and treatment. Substantial improvements in health care have been achieved by newly developed improved testing procedures which result in a determination in hours and in sometimes minutes after sample collection. These short duration tests do not rely on the collection and growth of microorganisms but look to identify chemical characteristics of the suspected biological substance such as an antigen which is associated with, for example, Streptococcus. Tests along these lines seek only to gather portions of the Streptococci, the antigen, and expose this biological sample to an antibody which is known to attach itself to the specific antigen. Accordingly, if the antigen is present the antibody will attach to it and a determination may be made. The prior art has taught attaching radioisotopes to antibodies so that if the antibody attaches to the antigen there will be a concentration of radioactive material at the attaching sites. This type of testing is known as a technique of a radioimmunoassay (RIA). Obviously, unattached antibodies must be removed so that only the combined antibody-antigen groups will remain. Antibodies have also been coupled with fluorochromes which are responsive to light and to enzymes which can react with additional substances to produce color changes and more recently to liposomes which contain color dyes.

In U.S. Pat. No. 4,618,576, Rosenstein et al. teach a test that can be performed in less than seventy minutes to determine the presence of Group A Streptococcus. Rosenstein et al. teach the use of a fiber swab on the end of a stick for swabbing the infected area to collect antigen in its fibers. Subsequently, the swab is dipped in a solution of extraction reagent containing enzymes which facilitate the release of the Streptococcus A antigen from the swab. Finally, an indicator reagent is provided with antibodies that are specifically reactive to the Streptococcus A antigen.

As technology allows the development of tests that are faster, it is more important to take the sample and deliver it to the test site in a timely manner. It may no longer be practical to have a fibrous swab or a tip containing interconnected cavities which trap the biological specimen thus requiring time to extract it from the interior of the swab or special solutions to promote the removal of the biological substance from the swab. Faster tests may be complemented with improved swab structures which allow the effective collection of a biological sample and its rapid transfer to the test system.

Also, traditional swabs having cotton or other fiber tips on rigid rod like shaft portions made of wood or plastic present potential problems due to the underlying sharp edges on rigid shaft portions which may irritate or injure the collection area if the sample is not properly and carefully taken. This potential for irritation is fibrous tip of the swab to provide complete protection from the sharp edge of the rod like wood or plastic shaft. Also, the straight shaft structure is not necessarily designed to be anatomically correct with respect to the portion of the patient body wherein the sample is being taken or with respect to the sample taker's hand. Bennett in U.S. Pat. No. 3,871,375 provides an improved structure wherein the open cell tip and the shaft portion of the swab are molded in the same cavity so that the blended region joining the central shaft and the soft, resilient tip merges gradually from the low porosity more rigid shaft portion to the high porosity soft resilient tip so that there is no sharp ended "stick" presented to the patient's body.

Although the prior art has addressed improved apparatus and tests for the taking of biological samples and the subsequent transfer and testing of these samples there is still a need for a simple, straight-forward, reliable, easily fabricated swab for collection of biological samples which provides for easier removal of the biological sample from the swabbing tip and improved structure, with respect to human factors, to improve the ease of sample gathering while minimizing the potential for irritation to the patient.

SUMMARY OF THE INVENTION

The swab for collecting biological samples of the present invention comprises a handle having a proximal end and a distal end. A swabbing tip formed of closed cell polymeric foam is provided at the distal end of the handle for contacting and collecting a biological sample.

Another embodiment of the swab for collection of biological samples of the present invention comprises a handle having a proximal portion including a proximal end and a distal portion including a distal end. The handle includes a shaft portion at the distal portion and a gripping portion at the proximal portion wherein the griping portion is more rigid than the shaft portion and the shaft portion is curvalinearly shaped. A swabbing tip formed of closed cell polymeric foam is provided at the distal end for contacting a biological sample. The swabbing tip includes surface discontinuity structure for facilitating biological sample gathering. The swabbing tip is softer and more resilient than the handle.

Another aspect of the present invention includes a method for collecting a biological sample comprising: (a) obtaining a swab including an elongate handle having a proximal portion including a proximal end and a distal end, and a swabbing tip formed of closed cell polymeric foam at the distal end; (b) grasping the handle at the proximal portion; (c) causing the swabbing tip to contact the area containing the biological material to be sampled so that a portion of the biological material is transferred to the swabbing tip; and (d) removing the swabbing tip from the area containing the biological material.

BRIEF DESCRIPTION OF THE DRAWINGS

FIG. 1 is a front elevation view of the preferred swab for collecting biological samples of the present invention;

FIG. 2 is a side elevation view of the swab for collecting biological samples of FIG. 1;

FIG. 3 is a rear elevation view of the swab for collecting biological samples of FIG. 1;

FIG. 4 is an enlarged partial cross-sectional view of the swab of FIG. 3 taken along line 4—4;

FIG. 5 is an enlarged cross-sectional view of the swab of FIG. 3 taken along line 5—5;

FIG. 6 is an enlarged cross-sectional view of the swab of FIG. 3 taken along line 6—6;

DETAILED DESCRIPTION

Figure 7:
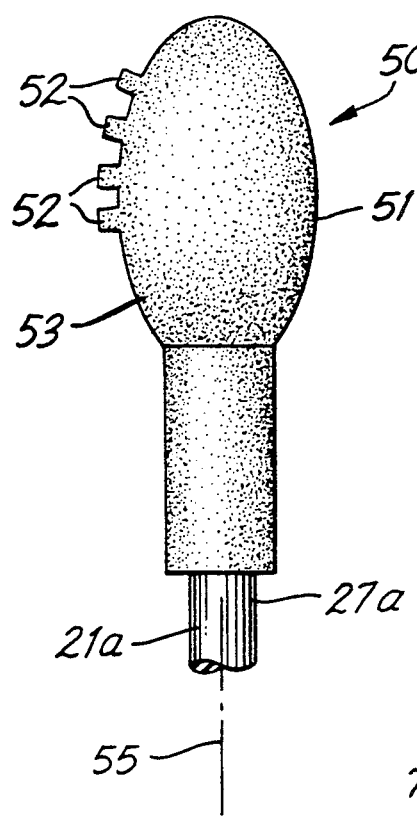
FIG. 7 is a partial side elevational view illustrating the swabbing tip of an alternative embodiment of the present invention.

While this invention is satisfied by embodiments in many different forms, there is shown in the drawings and will herein be described in detail preferred embodiments of the invention with the understanding that the present disclosure is to be considered as exemplary of the principles of the invention and not intended to limit the invention to the embodiments illustrated. The scope of the invention shall be measured by the appended claims and their equivalents.

Adverting to FIGS. 1 through 6, a preferred embodiment of the swab for collection of biological samples 20 includes a handle 21 having a proximal portion 22 including a proximal end 23 and a distal portion 25 including a distal end 27. For the purposes of the description of the present invention, the term "distal" is meant to refer to that end of the element which is furthest from the person holding the swab, whereas the term "proximal" is meant to refer to the end of the element closest to the holder of the swab.

Handle 21 includes a gripping portion 29 at the proximal portion and a shaft portion 31 at the distal portion. A feature of this embodiment is that gripping portion 29 is more rigid than shaft portion 31.

A swabbing tip 32 is provided at distal end 27 for contacting and collecting a biological sample. Swabbing tip 32 is formed of closed cell foam and is softer and more resilient than handle 21. It is preferred that the swabbing tip includes a convex surface for collection of biological samples. The convex shape is especially desirable when taking samples from body cavities such as a patient's throat wherein the rounded convex surface of the swabbing tip tends to be less irritating. However, since closed cell foam is used, the sample will remain substantially on the outside surface 33 of the swabbing tip. It is also desirable to have some form of surface discontinuity on the outside surface to facilitate the removal of the biological sample. In this preferred embodiment, the convex surface of the swabbing tip is spherically shaped and this surface includes a discontinuity for facilitating biological sample gathering in the form of concave grooves 34 having major axes running along their longer dimension. It is desirable, but not necessary, to orient these axes at an angle of between 45° and 90° with respect to a longitudinal axis 30 of the distal end of the handle. In this preferred embodiment, these axes are at an angle of about 90° with respect to longitudinal axis 30. Although the swabbing tip is convexly shaped and resilient to facilitate patient comfort the discontinuities provide a specific area on the surface of the swabbing tip which is more efficient for the purposes of gathering the biological sample.

In this preferred embodiment gripping portion 29 is curvalinearly shaped having a radius of curvature RG, as illustrated in FIG. 2. Also, the shaft portion 31 is curvalinearly shaped having a radius of curvature RS, as best illustrated in FIG. 2. In this preferred embodiment the origin of the radius of curvature for the gripping portion is opposed from the origin of the radius of curvature of the shaft portion so that the shaft portion appears convexly shaped when viewed from the origin of the radius of curvature of the gripping portion. In this preferred embodiment, a plane containing the shaft portion and the radius of curvature for the shaft portion is coextensive with a plane containing the gripping portion and the radius of curvature of the gripping portion. The curvalinearly shaped gripping portion and shaft portion are preferred but not a requirement of the invention. The curved gripping portion facilitates holding the handle while the reduced cross-section and curvalinear shape of the shaft portion provide a resiliency to minimize inadvertent irritation to the patient and to make it easier for the person taking the sample to access interior surfaces of the patient's body which are not in a straight line of sight from the exterior of the patient's body. The soft resilient swabbing tip and the resilient shaft portion are important features for controlling the pressure applied when taking the biological sample and minimizing inadvertent irritation to the patient.

Another feature of this preferred embodiment is means for facilitating holding the gripping portion and moving the swabbing tip while collecting a biological sample. In this preferred embodiment, this means includes external channels 37 on the gripping portion. Channels 37 are desirably oriented so that they extend across the longitudinal axis of the gripping portion. It will be apparent to one skilled in the art that numerous surface configurations can be used advantageously to facilitate holding the gripping portion for better control over the swabbing tip. These structures are within the purview of the instant invention and include, but are not limited to, parallel grooves or channels, a knurled surface having crossing grooves, a roughened surface to increase the coefficient friction and a coating over the gripping portion which is softer and more resilient to facilitate improved gripping.

In addition, the closed cell structure of the swabbing tip assures that the biological sample will remain substantially at the surface of the swabbing tip and in the discontinuities which are provided for holding the biological sample so that the task of removing the biological sample from the tip will be greatly simplified and additional steps or subjecting the tip to intermediate mixtures such as the use of an aqueous extraction reagent, as taught by Rosenstein et al. in U.S. Pat. No. 4,618,576, may be eliminated. An immunoassay test for determination of the presence of a specific biological substance cannot take place in minutes if substantially more time is required to remove the biological sample from the sampling device. The use of the closed cell foam to keep the biological sample at the surface of the swabbing tip and the use of the discontinuities to facilitate sample gathering is a clear and substantial advantage over prior art swabs.

In this preferred embodiment swabbing tip 32 includes a substantially cylindrical, closed end, passageway 38 which engages engaging structure 39 at distal end 27 of handle 21 for the purpose of securing swabbing tip 32 to handle 21. In this preferred embodiment engaging structure 39 includes a series of frusto conically shaped segments 40 oriented so that the swabbing tip may easily slip over the engaging structure with lower edges 41 of the frusto conically shaped segments resisting removal of the swabbing tip from the handle. The above-described structure for holding swabbing tip 32 onto handle 21 is preferred because it can eliminate the need for adhesives and other attachment means. It will be apparent to one skilled in the art that there are numerous means and structures for securing a closed cell foam swabbing tip to a more rigid handle structure including, but not limited to, adhesives, ultrasonic welding, complimentary engaging structure, external clamps and the like with the above-described structure being exemplary of these many possibilities.

In use the swab for collecting biological samples of the present invention is used in conjunction with immunoassay type tests which are designed to provide diagnostic information in a time frame of minutes rather than hours or days. These tests do not rely on the culturing of bacteria samples but upon a chemical reaction with a portion of the biological substance which is thought to be present, such as the antigen from Streptococcus bacteria, as described hereinabove. Accordingly, as will be described in more detail hereinafter, it is desirable to provide the swab in a package so that the swab is sterile at the time of use. The medical practitioner holds the swab of the present invention by gripping portion 29 and directs the swabbing tip toward the surface or area wherein the sample is to be taken, for example, the patient's throat. The curvature of the gripping portion and the shaft portion of the preferred embodiment of the swab for collection of biological samples of the present invention offers advantages in that it is more easily gripped and the curved shaft portion allows access to surfaces that may not be in the direct line of sights or which are difficult to access with a straight shaft-type handle of prior art devices. Also the relative resilience of the shaft portion and the convex surface of the swabbing tip minimize the possibility of irritation to the patient during the sample gathering procedure. The swab of the present invention can be positioned so that the swabbing tip is within the patient's throat and the swabbing tip maneuvered to contact the areas of suspected infection by moving the swabbing tip inwardly and outwardly in a direction perpendicular to the grooves in the swabbing tip to facilitate maximizing the quantity of sample gathered. The swabbing tip may then be removed from the patient's throat so that the collected sample may be transferred to a test device for subsequent analysis.

Referring now to FIG. 7, an alternative swab for the collection of biological samples 50 of the present invention includes components which are substantially identical to the components of the embodiment of FIGS. 1-6. Accordingly, similar components performing similar functions will be numbered identically to those components in the embodiment of FIGS. 1-6, except that the suffix "a" will be used to identify the components of FIG. 7. This alternative swab for the collection of biological samples includes a handle 21a having a distal end 27a and a proximal end (not shown). A swabbing tip is provided at distal end 27a for contacting and collecting a biological sample. Swabbing tip 51 is formed of closed cell foam and is softer and more resilient than handle 21a. It is preferred, but not necessary, that the swabbing tip have a convex surface for the collection of biological samples. In this embodiment, convex surface 53 of the swabbing tip is ellipsoidally shaped and this surface includes a discontinuity for facilitating biological sample gathering in the form of a plurality of raised protuberances 52 projecting outwardly from convex surface 53. The raised protuberances have major axes running along their longer dimension which in this embodiment places the major axes at an angle of about 90° with respect to the longitudinal axis 55 of distal end 27a. In other structural aspects the handle of the swab for the collection of biological samples of FIG. 7 is substantially similar to the handle of the embodiment of FIGS. 1-6.

Figure 8:
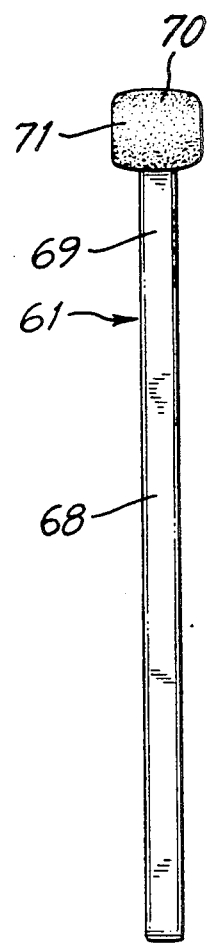
FIG. 8 is a front elevation view illustrating still another alternative embodiment of the present invention.
Figure 9:
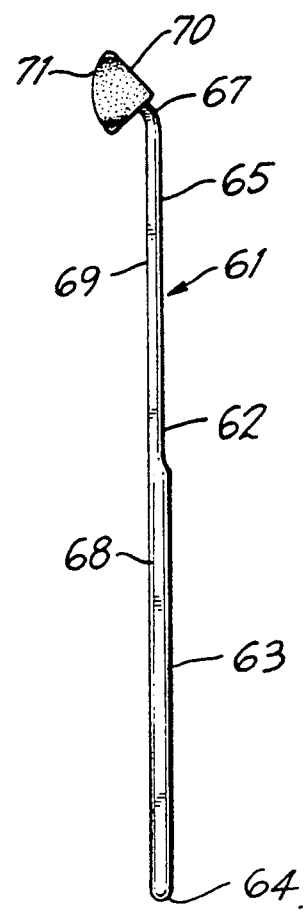
FIG. 9 is a side elevation view of the swab for collecting biological samples of FIG. 8.

Referring now to FIGS. 8 and 9 wherein an alternative swab for the collection of biological samples 61 is illustrated. Swab 61 includes a handle 62 having a proximal portion 63 including a proximal end 64 and a distal portion 65 having a distal end 67. Handle 62 also includes gripping portion 68 at the proximal portion and the shaft portion 69. In this embodiment the gripping portion 68 is more rigid than shaft portion 69.

A swabbing tip 70 is provided at distal end 67 for contacting and collecting a biological sample. Swabbing tip 70 is formed of closed cell foam and is softer and more resilient than handle 21. It is preferred that the swabbing tip have a convex surface 71 for the collection of biological samples.

A wide variety of rigid materials are suitable for the manufacture of the handle of the present invention including metal, wood, and plastic materials with thermoplastics being preferred because of the availability of manufacturing processes, such as injection molding, which allow the easy formation of a handle having the various shapes and surfaces described hereinabove. Thermoplastic materials such as polystyrene, polypropylene and polyethylene are preferred.

A wide variety of closed cell foam materials are suitable for the formation of the swabbing tip of the present invention with closed cell polyethylene foam being preferred. Such a closed cell polyethylene foam is available in formed parts from Illbruck/U.S.A. of Minneapolis, Minn. 55412, U.S.A. under the description of N-200 -A semi-rigid closed cell crosslinked polyethylene foam having a density of two (2) pounds per cubic foot (0.032 gram/cm$^3$). Closed cell foam may also be purchased in rectangular shapes and formed to the desired shape by the swab manufacturer. An important feature of the present swab for the collection of biological samples is the use of closed cell foam producing the benefits described hereinabove.

It can be seen that the present swab for the collection of biological samples provides a simple, straight forward, reliable, easily fabricated swab for the collection of biological samples which provides for easy removal of the biological sample from the swabbing tip and improved structure, with respect to human factors, to improve the ease of sample gathering while minimizing the potential for irritation to the patient.

What is claimed is:

1. A swab for collecting biological samples comprising:
    an elongate handle having a proximal portion including a proximal end and a distal portion including a distal end, said handle including a shaft portion at said distal portion and a gripping portion at said proximal portion wherein said gripping portion is more rigid than said shaft portion; and
    a swabbing tip at said distal end for contacting and collecting a biological sample, said swabbing tip being formed of closed cell polymeric foam, said swabbing tip being softer and more resilient than said handle, said swabbing tip including surface discontinuity means for facilitating biological sample gathering, said surface discontinuity means including at least one concave groove in the surface of said swabbing tip said shaft portion being resilient enough to deflect under forces applied to said swabbing tip while collecting biological samples in a patient's throat.

2. A swab for collecting biological samples comprising:
    an elongate handle having a proximal portion including a proximal end and a distal portion including a distal end, said handle including a shaft portion at said distal portion and a gripping portion at said proximal portion wherein said gripping portion is more rigid than said shaft portion; and
    a swabbing tip at said distal end for contacting and collecting a biological sample, said swabbing tip being formed of closed cell polymeric foam, said swabbing tip being softer and more resilient than said handle, said swabbing tip including surface discontinuity means for facilitating biological sample gathering, said surface discontinuity means including at least one protuberance projecting outwardly from the surface of said swabbing tip said shaft portion being resilient enough to deflect under forces applied to said swabbing tip while collecting biological samples in a patient's throat.

3. A swab for collecting biological samples comprising:
    an elongate handle having a proximal portion including a proximal end and a distal portion including a distal end, said handle including a shaft portion at said distal portion and a gripping portion at said proximal portion wherein said gripping portion is more rigid than said shaft portion, said gripping portion including gripping means for facilitating holding said gripping portion and controlling the position of said swabbing tip while collecting a biological sample, said gripping means including a plurality of external channels on said gripping portion; and
    a swabbing tip at said distal end for contacting and collecting a biological sample, said swabbing tip being formed of closed cell polymeric foam, said swabbing tip being softer and more resilient than said handle, said shaft portion being resilient enough to deflect under forces applied to said swabbing tip while collecting biological samples in a patient's throat.

4. A method for collecting biological samples in a patient's throat comprising:
    (a) obtaining a swab including an elongate handle having a proximal portion including a proximal end and a distal portion including a distal end, and a swabbing tip formed of closed cell polymeric foam at said distal end;
    (b) grasping said handle at said proximal portion;
    (c) causing the swabbing tip to contact the area of said patient's throat containing the biological material to be sampled so that a portion of said biological material is transferred to said swabbing tip; and
    (d) removing the swabbing tip from said area containing the biological material.

5. The method of collecting biological samples of claim 4 wherein said closed cell polymeric foam is polyethylene foam.

6. The method of collecting biological samples of claim 4 wherein said swabbing tip is sterile.

7. The method for collecting biological samples of claim 4 wherein said swabbing tip includes a convexly shaped surface portion.

8. The method for collecting biological samples of claim 4 wherein said swabbing tip includes an ellipsoidally shaped surface portion.

9. The method for collecting biological samples of claim 4 wherein said swabbing tip includes a spherically shaped surface portion.

10. The method for collecting biological samples of claim 4 wherein said swabbing tip includes surface discontinuity means for facilitating biological sample gathering.

11. The method for collecting biological samples of claim 10 wherein said surface discontinuity means has an elongate shape having a major axis running along its longer dimension.

12. The method for collecting biological samples of claim 11 wherein said major axis is at an angle within the range of about 45° to 90° with respect to the elongate handle at said distal end.

13. The method for collecting biological samples of claim 10 wherein said surface discontinuity means includes at least one concave groove in the surface of said swabbing tip.

14. The method for collecting biological samples of claim 10 wherein said surface discontinuity means includes at least one protuberance projecting outwardly from the surface of said swabbing tip.

15. The method for collecting biological samples of claim 4 wherein said handle includes a shaft portion at said distal portion and a gripping portion at said proximal portion wherein said gripping portion is more rigid than said shaft portion.

16. The method for collecting biological samples of claim 15 wherein said shaft portion is curvalinearly shaped.

17. The method for collecting biological samples of claim 15 wherein said gripping portion is curvalinearly shaped.

18. The method for collecting biological samples of claim 15 wherein said shaft portion is curvalinearly shaped and said gripping portion is curvalinearly shaped.

19. The method for collecting biological samples of claim 18 wherein a plane containing said shaft portion and a radius of curvature for said shaft portion is coextensive with a plane containing said gripping portion and a radius of curvature of said gripping portion.

20. The method for collecting biological samples of claim 18 wherein said shaft portion is convexly shaped when viewed from the origin of the radius of curvature of said gripping portion.

21. The method for collecting biological samples of claim 18 wherein the origin of a radius of curvature of said shaft portion is opposed from the origin of a radius of curvature of said gripping portion.

22. The method for collecting biological samples of claim 15 wherein said gripping portion has a substantially rectangular cross section.

23. The method for collecting biological samples of claim 15 wherein said gripping portion includes gripping means for facilitating holding said gripping portion and controlling the position of said swabbing tip while collecting the biological sample.

24. The method for collecting biological samples of claim 23 wherein said gripping means includes a plurality of external channels on said gripping portion.

25. The method for collecting biological samples of claim 5 wherein said foam has a density of substantially about 2 pounds per cubic foot.

* * * * *